(12) United States Patent
Blanchard et al.

(10) Patent No.: US 11,590,323 B2
(45) Date of Patent: Feb. 28, 2023

(54) CATHETER ASSEMBLY SUPPORT DEVICE, SYSTEMS, AND METHODS

(71) Applicant: Becton, Dickinson and Company, Franklin Lakes, NJ (US)

(72) Inventors: Curtis H. Blanchard, Riverton, UT (US); Tyler Warner, Bluffdale, UT (US); Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 173 days.

(21) Appl. No.: 16/866,262

(22) Filed: May 4, 2020

(65) Prior Publication Data

US 2020/0360668 A1 Nov. 19, 2020

Related U.S. Application Data (60) Provisional application No. 62/847,084, filed on May 13, 2019.

(51) Int. Cl.
| | |
|---|---|
| *A61M 25/02* | (2006.01) |
| *A61M 25/06* | (2006.01) |
| *A61M 39/10* | (2006.01) |
| *A61M 39/22* | (2006.01) |
| *A61M 39/24* | (2006.01) |

(52) U.S. Cl.
CPC ........ *A61M 25/02* (2013.01); *A61M 25/0606* (2013.01); *A61M 39/10* (2013.01); *A61M 39/22* (2013.01); *A61M 2039/248* (2013.01)

(58) Field of Classification Search
CPC .. A61M 25/02; A61M 25/0606; A61M 39/10; A61M 39/22; A61M 2039/248

USPC .......................................................... 604/174
See application file for complete search history.

(56) References Cited

U.S. PATENT DOCUMENTS

| | | | |
|---|---|---|---|
| 3,794,032 | A | 2/1974 | Derouineau |
| 3,826,256 | A | 7/1974 | Smith |
| 5,176,662 | A | 1/1993 | Bartholomew et al. |
| 5,865,808 | A | 2/1999 | Corn |

(Continued)

FOREIGN PATENT DOCUMENTS

| | | |
|---|---|---|
| EP | 434324 | 6/1991 |
| EP | 2992843 | 3/2016 |
| WO | 2010/132837 | 11/2010 |

*Primary Examiner* — Phillip A Gray
(74) *Attorney, Agent, or Firm* — Kirton McConkie; Whitney Blair; Kevin Stinger (57) ABSTRACT

A support device to support a catheter assembly may include a platform, which may include an upper surface and a bottom surface. The support device may include an extension element coupled to the upper surface of the platform. The extension element may include a distal end, which may include a first connector configured to couple to the catheter assembly, and a proximal end, which may include a second connector. The extension element may include a valve that may be movable between a first position and a second position. In response to the valve being moved to the first position, a fluid pathway extending through the cannula and the extension element may be open and straight. In response to the valve being moved to the second position, the fluid pathway may be closed. The support device may include a cannula, which may be swaged within the extension element.

16 Claims, 11 Drawing Sheets

(56) References Cited

U.S. PATENT DOCUMENTS

2009/0143764 A1 6/2009 Nelson
2018/0154112 A1* 6/2018 Chan ................. A61M 25/0097

* cited by examiner

CATHETER ASSEMBLY SUPPORT DEVICE, SYSTEMS, AND METHODS

RELATED APPLICATIONS

This application claims the benefit of U.S. Provisional Application No. 62/847,084, filed May 13, 2019, and entitled CATHETER ASSEMBLY SUPPORT DEVICE, SYSTEMS, AND METHODS which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and introducer needle are generally inserted at a shallow insertion angle through the skin into vasculature of the patient.

In order to verify proper placement of the introducer needle and/or the PIVC in the blood vessel, a clinician generally confirms that there is "flashback" of blood in a flashback chamber of a PIVC assembly. Once placement of the needle has been confirmed, the clinician may temporarily occlude flow in the vasculature and remove the introducer needle, leaving the PIVC in place for future blood withdrawal and/or fluid infusion.

Placement of the PIVC within the vasculature is essential for blood withdrawal and fluid infusion and yet may be difficult to maintain. Patients often want or need to have a normal range of body motion while the PIVC is inserted. Also, external objects may apply external forces to the PIVC and thereby shift the PIVC's location within the vasculature. In some instances, the external forces may cause back-and-forth dynamic movement of a tip of the PIVC or a static shift in the tip from its location within the vasculature.

The PIVC assembly may be coupled with an extension set, which may allow coupling of an infusion or blood withdrawal device at a location removed from an insertion site of the PIVC. While the extension set may reduce a risk of disturbing the insertion site or dislodging the catheter from the vasculature of the patient, the risk may still remain.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to support devices and related systems and methods. In some embodiments, the present disclosure relates to support devices that may support a catheter assembly. In some embodiments, a support device may include a platform, which may include an upper surface and a bottom surface. In some embodiments, the bottom surface may be configured to contact skin of a patient and/or at least a portion of the upper surface may be configured to support the catheter assembly. In some embodiments, the support device may include an extension element, which may be coupled to the upper surface of the platform. In some embodiments, the extension element may include a distal end and a proximal end. In some embodiments, the distal end may include a first connector configured to couple to the catheter assembly. In some embodiments, the proximal end of the extension element may include a second connector.

In some embodiments, the extension element may include a valve, which may be disposed between the distal end of the extension element and the proximal end of the extension element. In some embodiments, the valve may be movable between a first position and a second position. In some embodiments, the support device may include a cannula, which may extend distally from the distal end of the extension element and may be secured within the extension element. In some embodiments, in response to the valve being moved to the first position, a fluid pathway extending through the cannula and the extension element may be open and/or straight. In some embodiments, in response to the valve being moved to the second position, the fluid pathway may be closed.

In some embodiments, the valve may include a socket and an arm. In some embodiments, the arm may include a distal end, a proximal end, and a lumen extending through the distal end of the arm and the proximal end of the arm. In some embodiments, the distal end of the arm may include a ball portion, which may be configured to rotate within the socket. In some embodiments, the proximal end of the arm may include the second connector. In some embodiments, the ball portion may be generally spherical. In some embodiments, the distal end of the arm may include one or more flat surfaces.

In some embodiments, an outer surface of the ball portion may include a protrusion and/or the socket may include a slot. In some embodiments, the slot may include a first end and a second end. In some embodiments, in response to the valve being moved to the first position, the protrusion may be disposed at the first end of the slot. In some embodiments, in response to the valve being moved to the second position, the protrusion may be disposed at the second end of the slot.

In some embodiments, the slot may include a neck portion, which may include a narrowed diameter. In some embodiments, in response to the valve being moved to the first position from the second position and/or from the second position to the first position, the protrusion may pass through the neck portion, which may provide an audible and/or tactile indication.

In some embodiments, the socket may include one or more protrusions, which may contact an outer surface of the arm. In some embodiments, the protrusions may be configured to provide resistance in moving the valve between the first position and the second position.

In some embodiments, the cannula may include a distal end, a proximal end, and a lumen extending through the distal end of the cannula and the proximal end of the cannula. In some embodiments, the proximal end of the cannula may include a wedge. In some embodiments, the cannula may be swaged into the extension element. In some embodiments, the wedge may provide a fluid seal after the cannula is swaged into the pocket. In some embodiments, forming the wedge at the proximal end of the cannula may include deep drawing, stamping, coating, or three-dimensional printing. In some embodiments, an outer surface of the cannula between the distal end of the cannula and the proximal end of the cannula may include a protrusion, which may be configured to secure the cannula within the extension element or to secure the cannula within the catheter assembly.

In some embodiments, the distal end of the arm may include a generally cylindrical shape, which may be configured to rotate within the socket. In some embodiments, the socket may be generally cylindrical. In some embodiments, the proximal end of the arm may include the second connector. In some embodiments, the valve may include a handle, which may be disposed on an exterior surface of the valve. In some embodiments, in response to rotation of the handle a predetermined amount, the valve may move between the first position and the second position.

In some embodiments, the platform of the support device may be wedge-shaped. In some embodiments, the portion of the upper surface may include a groove configured to support a catheter adapter of the catheter assembly. In some embodiments, the first connector may include a snap feature, which may include an arm. In some embodiments, the arm may include a protrusion configured to engage in a snap fit with a groove of the catheter adapter.

In some embodiments, a method of securing the cannula may include providing the cannula. In some embodiments, the method of securing the cannula may include forming the wedge at the proximal end of the cannula. In some embodiments, the method of securing the cannula may include providing a medical device, which may include a pocket configured to receive the proximal end of the cannula. In some embodiments, the medical device may include the support device. In some embodiments, the medical device may include a syringe. In some embodiments, the method of securing the cannula may include inserting the proximal end of the cannula into the pocket and swaging the proximal end of the cannula into pocket. In some embodiments, the extension element may include the pocket, which may be disposed between the distal end of the extension element and the proximal end of the extension element.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
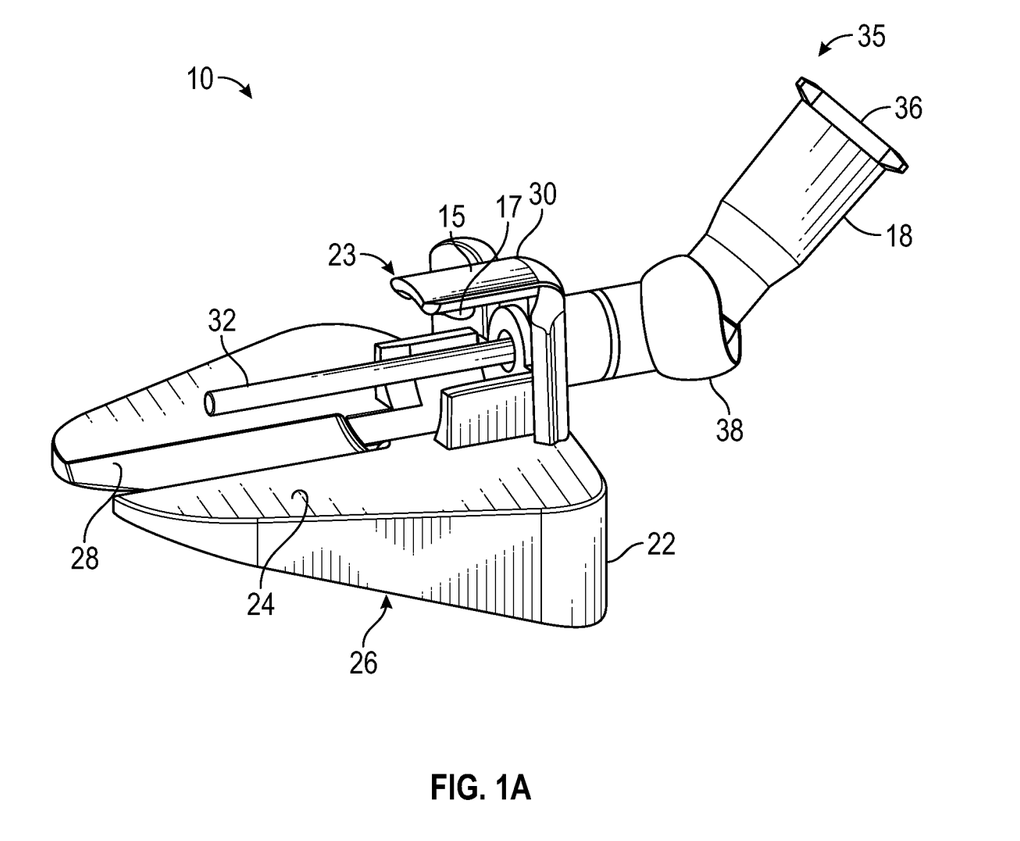
FIG. 1A is an upper perspective view of an example support device, illustrating an example extension element and example valve, according to some embodiments.
Figure 1B:
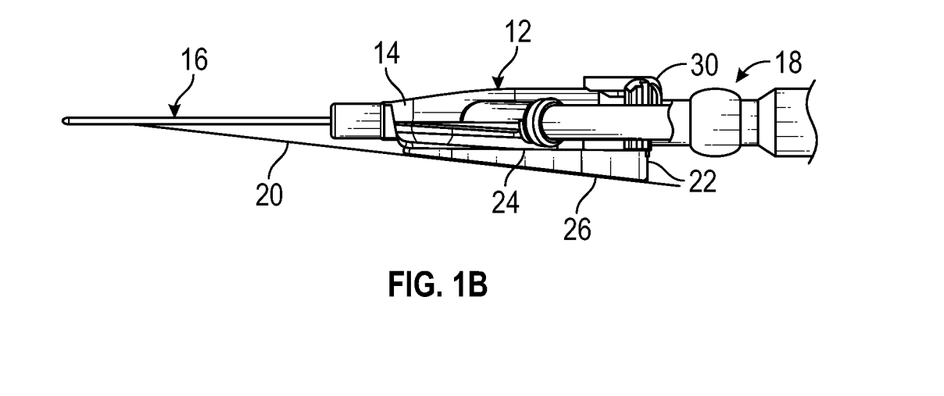
FIG. 1B is a side-view of the support device of FIG. 1A, illustrating an example catheter assembly coupled to the support device, according to some embodiments.
Figure 1C:
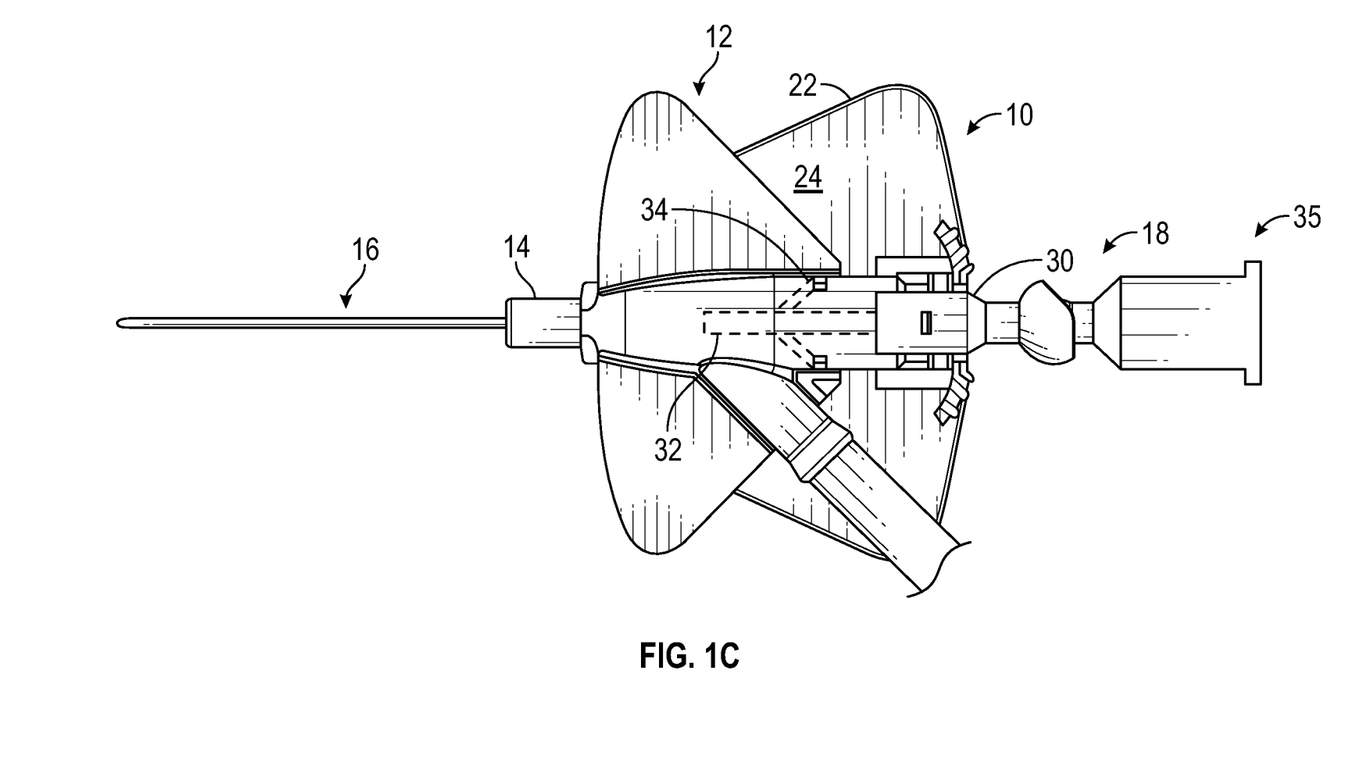
FIG. 1C is a top view of the support device and catheter assembly, according to some embodiments.

Referring now to FIGS. 1A-1C, a support device 10, which may support a catheter assembly 12, is illustrated, according to some embodiments. In some embodiments, the support device 10 may be coupled to a proximal end of the catheter assembly 12 and may support the catheter assembly 12 at an angle with respect to skin of a patient.

In some embodiments, the catheter assembly 12 may include a catheter adapter 14 and a catheter 16. In some embodiments, the catheter 16 may be secured within the catheter adapter 14 and may extend distally from a distal end of the catheter adapter 14. In some embodiments, the catheter 16 may include a peripheral intravenous catheter ("PIVC"), a peripherally inserted central catheter ("PICC"), or a midline catheter. In some embodiments, the catheter assembly 12 may be integrated with an integrated extension tube or non-integrated with an extension tube.

In some embodiments, in order to place the catheter 16 within vasculature of the patient for fluid infusion and/or blood withdrawal, an introducer needle (not illustrated) and the catheter 16 may be inserted into the skin 20 of the patient at a shallow insertion angle with respect to the skin 20. In some embodiments, the insertion angle may be about 30° or less. In some embodiments, the introducer needle may be removed following confirmation that the catheter 16 is in the vasculature. In some embodiments, after the introducer needle is removed, the catheter assembly 12 may be coupled to the support device 10. In some embodiments, the support device 10 may be coupled to the proximal end of the catheter adapter 14. In some embodiments, the support device 10 may be integrated with or monolithically formed as a single unit with the proximal end of the catheter adapter 14.

In some embodiments, the support device 10 may include a platform 22. In some embodiments, the platform 22 may include an upper surface 24 and a bottom surface 26. In some embodiments, the bottom surface 26 may be configured to contact the skin 20 of a patient to support the catheter assembly 12. In some embodiments, the bottom surface 26 of the platform 22 may be generally planar and may sit flat against the skin 20. In some embodiments, at least a portion of the upper surface 24 of the platform 22 may be angled with respect to the bottom surface 26 and/or the skin 20. In some embodiments the platform 22 may be wedge-shaped. In some embodiments, the portion of the upper surface 24 may be configured to support the catheter adapter 14 at an angle equal to or less than the insertion angle of the catheter 16.

In some embodiments, the portion of the upper surface 24 of the platform 22 may support the catheter assembly 12 in a position with the distal end or nose of the catheter adapter 14 tilted downward toward the skin 20 of the patient and the proximal end of the catheter adapter 14 tilted upward away from the skin 20 of the patient, which may facilitate insertion of an instrument through the support device 10 and/or into the vasculature. In some embodiments, the instrument may include an additional catheter for fluid infusion or blood draw, a guidewire, a probe with a sensor, or a light tube for disinfection.

In some embodiments, the upper surface 24 may include a groove 28, which may be aligned with a longitudinal axis of the support device 10. In some embodiments, the catheter adapter 14 may rest within the groove 28. In some embodiments, a thickness of the support device 10 at a proximal end of the groove 28 may be greater than a thickness of the support device 10 at a distal end of the groove 28 such that groove 28 may support the catheter adapter 14 at an angle for insertion of an introducer needle into the vasculature of the patient.

In some embodiments, at least a portion of the support device 10 may be constructed of a rigid material. In some embodiments, at least a portion of the support device 10, such as, for an example, the platform 22, may be constructed of a soft, flexible material, which may conform to the skin of the patient.

In some embodiments, the support device 10 may include an extension element 18, which may be coupled to the upper surface 24 of the platform 22. In some embodiments, the extension element 18 may be coupled to a proximal portion or end of the platform 22. In some embodiments, the extension element 18 may be monolithically formed as a single unit with the platform 22. In some embodiments, the extension element 18 may improve patient comfort and may decrease a risk of disturbance of an insertion site of the catheter 16 by moving a connection site of an infusion or blood withdrawal device away from the insertion site.

In some embodiments, the extension element 18 may include a distal end 23, which may include a first connector 30. In some embodiments, the first connector 30 may be configured to couple to the catheter assembly 12. In some embodiments, the support device 10 may be coupled to the catheter adapter 14 in a snap fit. In some embodiments, the first connector 30 may include a snap feature or another suitable coupling mechanism to couple the support device 10 to the proximal end of the catheter adapter 14. In some embodiments, the snap feature may include one or more arms 15, which may each include a protrusion 17 configured to be positioned within a groove of the catheter adapter 14 when the support device 10 is coupled to the catheter adapter 14 in the snap fit.

In some embodiments, the extension element 18 may include a cannula 32, which may extend distally from the distal end 23 of the extension element 18. In some embodiments, the cannula 32 may be secured within the support device 10. In some embodiments, the cannula 32 may extend parallel to the portion of the upper surface 24 of the platform 22. In some embodiments, the cannula 32 may be axially aligned with a longitudinal axis or fluid pathway of the catheter assembly 12.

In some embodiments, the cannula 32 may include a blunt cannula, which may be configured to extend through a proximal opening of the proximal end of the catheter adapter 14 and penetrate a blood control septum 34 disposed within a lumen of the catheter adapter 14. In some embodiments, the catheter adapter 14 may include a blood control septum 34, which may be multi-use or single-use.

In some embodiments, the extension element 18 may include a proximal end 35, which may include a second connector 36. In some embodiments, the second connector 36 may include a luer adapter, such as a male or female luer adapter. In some embodiments, the second connector 36 may include a slip or thread luer adapter or another suitable connector.

In some embodiments, the extension element 18 may include a valve 38, which may be disposed between the distal end 23 of the extension element 18 and the proximal end 35 of the extension element 18. In some embodiments, the valve 38 may be movable between a first position and a second position. In some embodiments, the valve 38 may provide a means of closing a fluid pathway 40 to an external environment, which may prevent bacteria from entering the extension element 18.

Figure 2A:
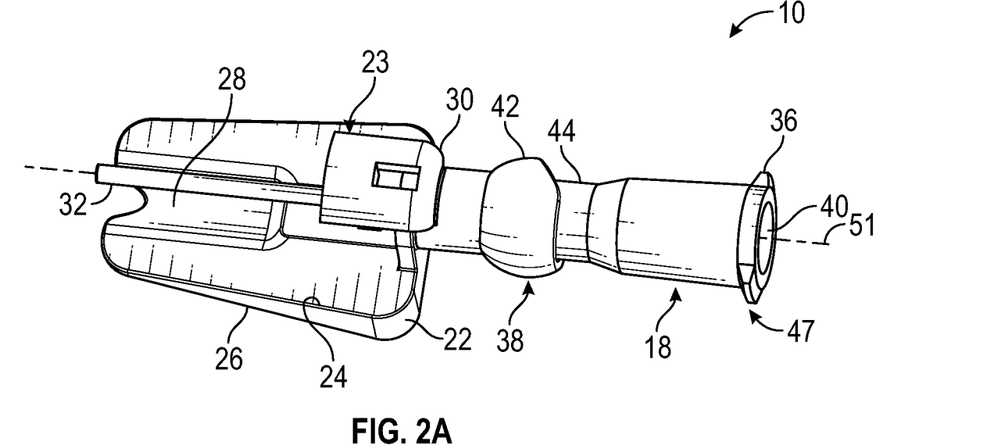
FIG. 2A is an upper perspective view of the support device of FIG. 1A, according to some embodiments.
Figure 2B:
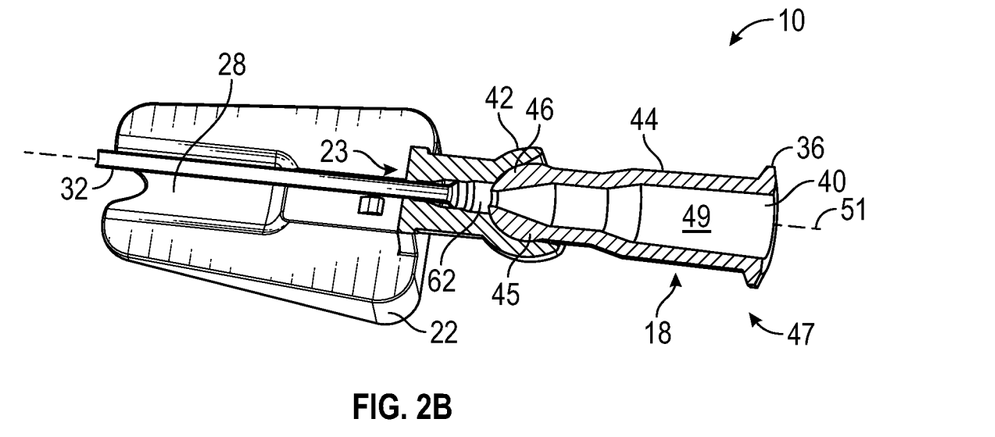
FIG. 2B is a cross-sectional view of the support device of FIG. 1A, illustrating the valve in an example first position, according to some embodiments.
Figure 2C:
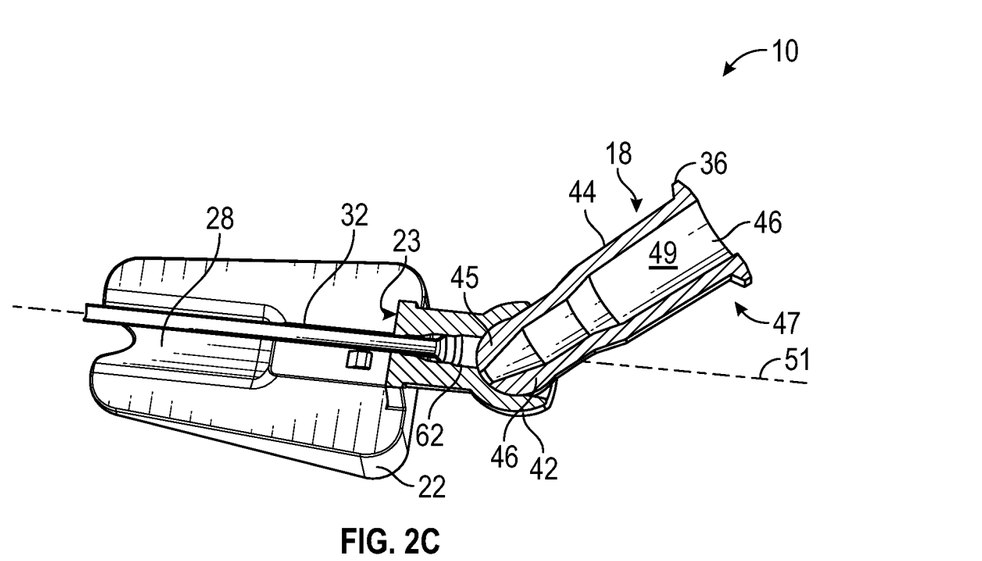
FIG. 2C is a cross-sectional view of the support device of FIG. 1A, illustrating the valve in an example second position, according to some embodiments.

Referring now to FIGS. 2A-2C, in some embodiments, valve 38 may be moveable between the first position, as illustrated, for example, in FIGS. 2A-2B, and the second position, as illustrated, for example, in FIG. 2C. In some embodiments, in response to the valve 38 being in the first position, the fluid pathway 40 extending through the cannula 32 and the extension element 18 may be open and straight, which may allow fluid flow and/or instrument access. In some embodiments, in response to the valve 38 being moved to the second position, the fluid pathway 40 may be closed.

In some embodiments, the valve 38 may include a socket 42 and an arm 44. In some embodiments, the arm 44 may include a distal end 45, a proximal end 47, and a lumen 49 extending through the distal end 45 of the arm 44 and the proximal end 47 of the arm 44. In some embodiments, the fluid pathway 40 may include the lumen 49. In some embodiments, the distal end 45 of the arm 44 may include a ball portion 46, which may include a generally spherical outer surface. In some embodiments, the ball portion 46 may be configured to rotate within the socket 42, which may include a generally spherical inner surface. In some embodiments, the proximal end 47 of the arm 44 may include the second connector 36.

In some embodiments, the ball portion 46 may freely rotate within the socket 42. In some embodiments, the ball portion 46 at the distal end of the arm 44 may fit into the socket 42 such that the arm 44 is capable of motion around many axes with one common center. In some embodiments, the socket 42 and the ball portion 46 may fit together snugly to prevent or minimize fluid leakage through the valve 38 from the fluid pathway 40.

In some embodiments, in response to the valve 38 being in the first position, the fluid pathway 40 may be generally straight or aligned with the longitudinal axis 51 of the support device 10. In these and other embodiments, the valve 38 may be open for fluid to pass through the valve 38 and through the catheter adapter 14. In some embodiments, in response to the valve 38 being in the second position, the fluid pathway 40 may be closed such that fluid is not able to pass through the valve 38. In some embodiments, the fluid pathway 40 may include features such as diameter changes, slopes, protrusions, or annular spacers that may guide the instrument through the fluid pathway 40 and into the catheter adapter 14 and may reduce or eliminate any catches.

In some embodiments, in response to the valve 38 being in the second position, the arm 44 may be angled with respect to the longitudinal axis 51. For example, in response to the valve 38 being in the second position, the arm 44 may be angled between 0° and 90° or between 30° and 60° with respect to the longitudinal axis 51.

Figure 3A:
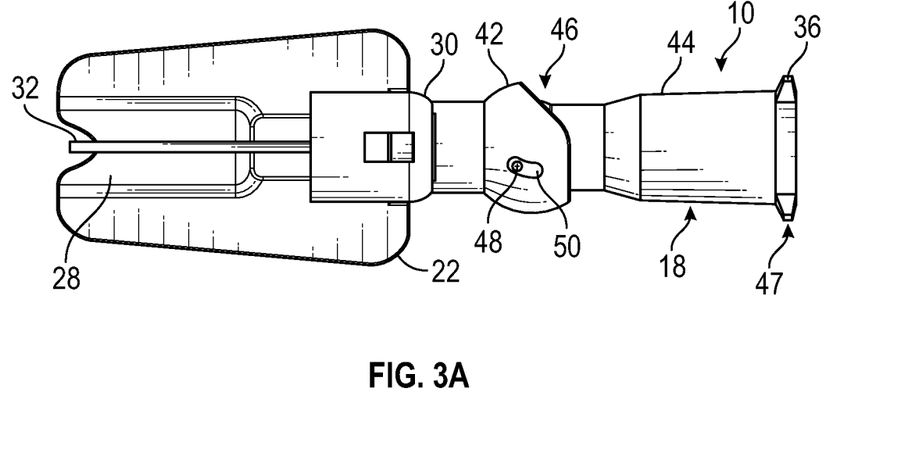
FIG. 3A is an upper perspective view of the support device of FIG. 1A, illustrating the valve in the first position and an example alignment mechanism, according to some embodiments.
Figure 3B:
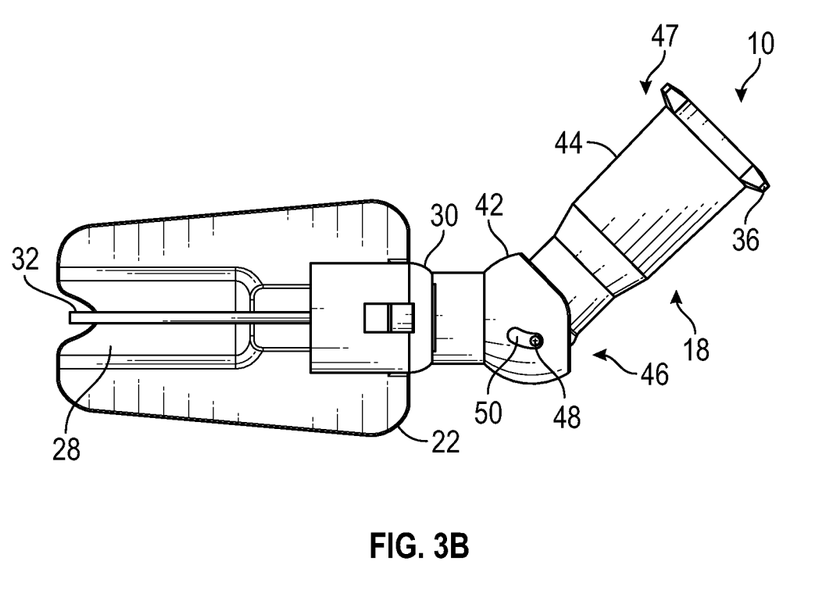
FIG. 3B is another upper perspective view of the support device of FIG. 1A, illustrating the valve in the second position and the alignment mechanism, according to some embodiments.

Referring now to FIGS. 3A-3B, in some embodiments, an outer surface of the arm 44 may include a protrusion 48. In some embodiments, the ball portion 46 may include the protrusion 48. In some embodiments, the socket 42 may include a slot 50, which may include a first end and a second end. In some embodiments, in response to the valve 38 being moved to the first position, the protrusion 48 may be disposed at the first end of the slot 50, as illustrated, for example, in FIG. 3A. In some embodiments, in response to the valve 38 being moved to the second position, the protrusion 48 may be disposed at the second end of the slot 50, as illustrated, for example, in FIG. 3B. It is understood that, in some embodiments, an inner surface of the socket 42 may include the protrusion 48, and the outer surface of the arm 44 may include the slot 50.

In some embodiments, the protrusion 48 and the slot 50 may be visible to a clinician on the socket 42 of the valve 38. In some embodiments, the protrusion 48 and the slot 50 may not be visible to the clinician. In some embodiments, the slot 50 may include a hole, which may extend through the socket 42, as illustrated, for example, in FIGS. 3A-3B. In other embodiments, the slot 50 may include a groove or indent which may not extend through the socket 42. In some embodiments, the slot 50 may be generally U-shaped or curved.

In some embodiments, the protrusion 48 and slot 50 provide an alignment mechanism for the socket 42 and the ball portion 46, which may limit a range of motion of the arm 44. In some embodiments, the protrusion 48 may be proximate or contacting the first end of the slot 50 when the valve 38 is in the first position. In some embodiments, the protrusion 48 may be proximate or contacting the second end of the slot 50 when the valve 38 is in the second position. Thus, in some embodiments, the protrusion 48 and the slot 50 may limit motion of the arm 44 away from the longitudinal axis 51 beyond the second position.

Figure 3C:
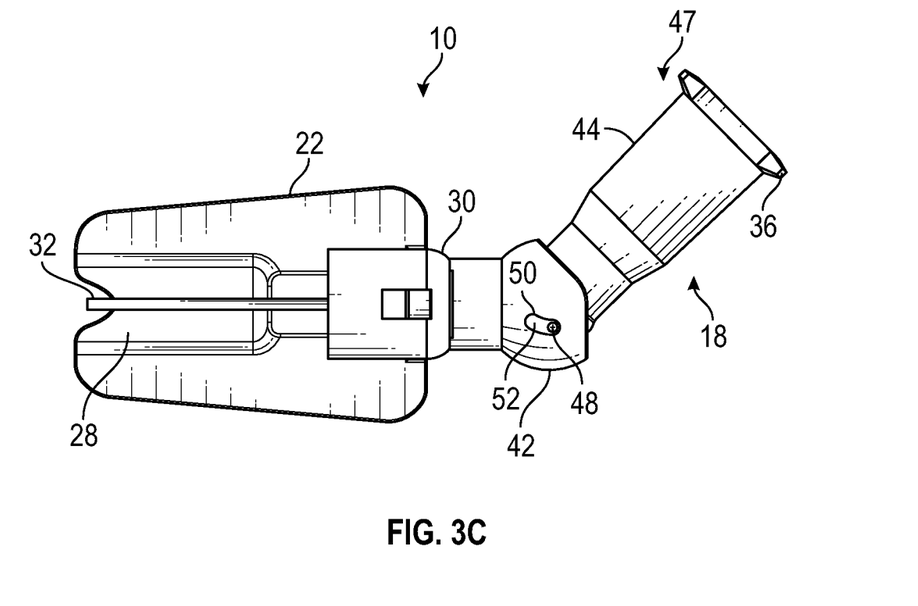
FIG. 3C is another upper perspective view of the support device of FIG. 1A, illustrating an example a neck portion, according to some embodiments.

Referring now to FIG. 3C, in some embodiments, the slot 50 may include a neck portion 52. In some embodiments, the neck portion 52 may include a narrowed diameter, which may be formed by two protrusions across from each other on the opposite sides of the slot 50. In some embodiments, in response to the valve 38 being moved to the first position and/or the second position, the protrusion 48 may pass through the neck portion 52, which may provide an audible and/or tactile indication. In some embodiments, the audible indication may include a click noise. In some embodiments, the audible and/or tactile indication may indicate to the clinician or a patient that the valve 38 is in the first position and/or the second position.

Figure 3D:
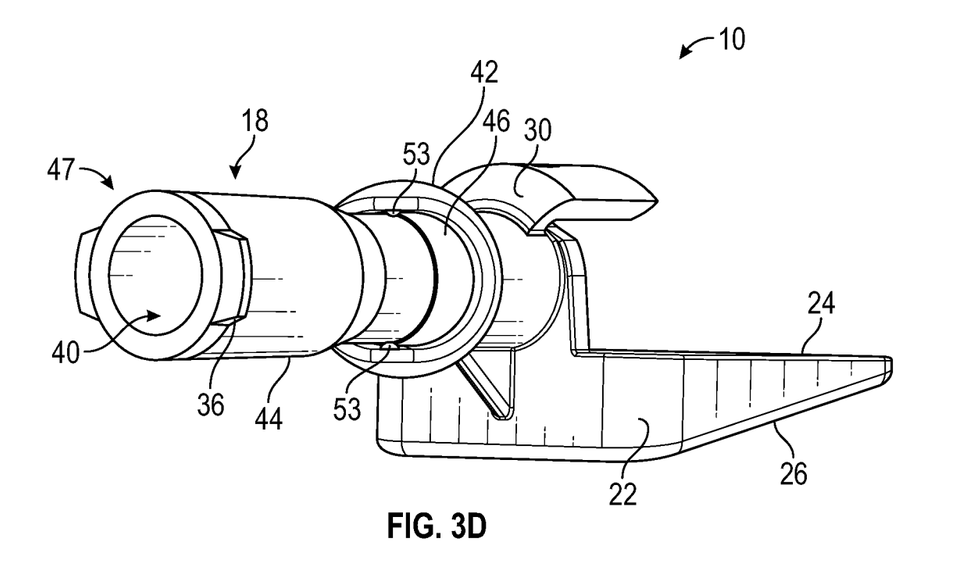
FIG. 3D is an upper perspective view of the proximal end of support device of FIG. 1A, illustrating example protrusions that may contact an outer surface of an example arm of the extension element, according to some embodiments.

Referring now to FIG. 3D, in some embodiments, one or more bumps or protrusions 53 may be disposed between the socket 42 and the arm 44. In some embodiments, the socket 42 may include one or more bumps or protrusions 53, which may contact the outer surface of the arm 44. In some embodiments, the protrusions 53 may be configured to provide resistance in moving the valve 38 between the first position and the second position, which may prevent inadvertent movement of the valve 38. In some embodiments, a particular protrusion 53 may be disposed opposite another particular protrusion 53. In some embodiments, the arm 44 may include the protrusions 53.

Figure 3E:
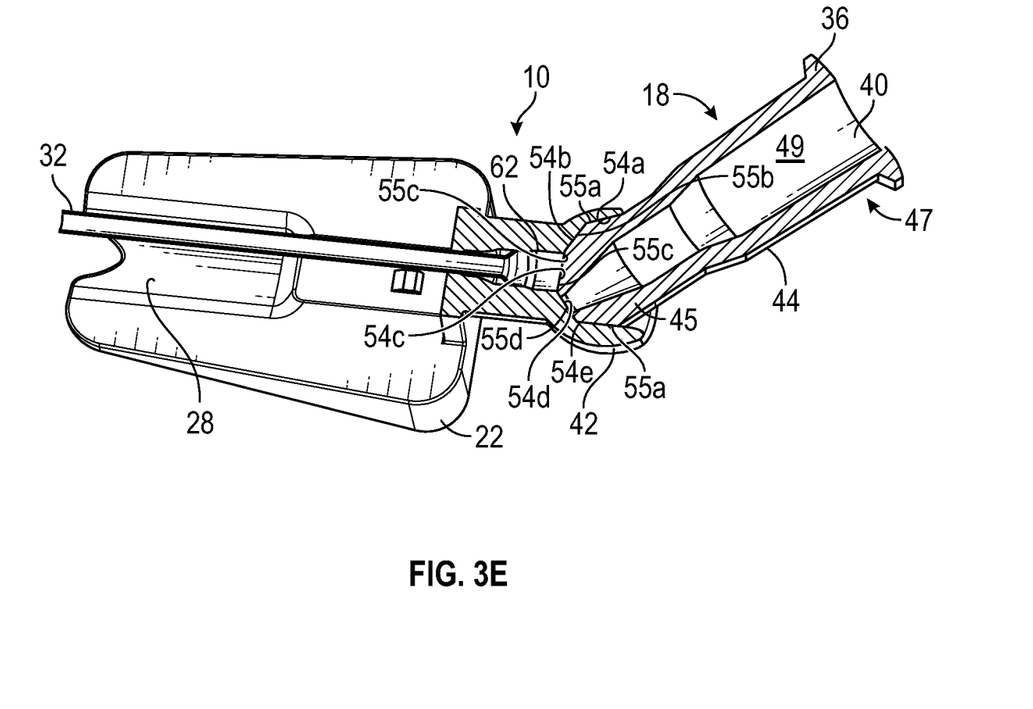
FIG. 3E is a cross-sectional view of the support device of FIG. 1A, illustrating another example valve, according to some embodiments.

Referring now to FIG. 3E, in some embodiments, the distal end 45 of the arm 44 may include one or more flat surfaces 54. In some embodiments, the socket 42 may also include one or more other flat surfaces 55, which may move with respect to the flat surfaces 54 to move the valve 38 between the first position and the second position. In some embodiments, the flat surfaces 54 of the arm 44 and the flat surfaces 55 of the socket 42 may contact each other and provide resistance to further motion.

In some embodiments, in response to the valve 38 being in the first position, a particular flat surface 54 may be aligned with the fluid pathway 40. In some embodiments, in response to the valve 38 being in the second position, the particular flat surface 54 may not be aligned with the fluid pathway 40, and the valve 38 may be shut. In some embodiments, the flat surfaces 54 of the ball portion 46 and/or other flat surfaces 55 of the socket 42 may act as a series of discrete positions for the arm 44 and/or the valve 38. In some embodiments, the flat surfaces 54 and the other flat surfaces 55 may provide a finite number of positions for the arm 44.

In some embodiments, the distal end 45 may include a handle 58 (see, for example, FIG. 4A), which may be disposed on an exterior surface of the valve 38. In response to rotation of the handle 58 a predetermined amount, the valve 38 may move between the first position and the second position. In some embodiments, the distal end 45 may include a position indicator (not illustrated) disposed on an exterior surface of the distal end 45 to provide an indication of the position of the valve 38. In some embodiments, the protrusion 48 and a position of the protrusion 48 in the slot 50 may provide an indication of the position of the valve 38.

Figure 4A:
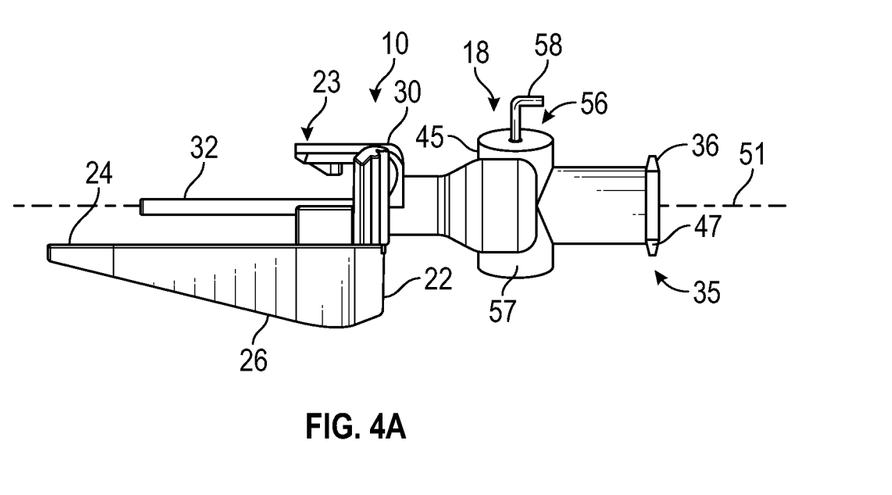
FIG. 4A is a side view of the support device of FIG. 1A, illustrating another example valve, according to some embodiments.

Referring now to FIG. 4A, in some embodiments, the extension element 18 may include a valve 56. In some embodiments, the valve 56 may include or correspond to the valve 38. In some embodiments, the distal end 45 of the arm 44 of the valve 56 may include a cylinder portion 57, as opposed to the ball portion 46. In some embodiments, in response to rotation of the cylinder portion 57 within the socket 42, the valve 56 may move between the first position and the second position, which may include or correspond to the first position and the second position, respectively, of the valve 38. In some embodiments, an inner surface of the socket 42 may be generally cylindrical and may contact the cylinder portion 57 to prevent leakage.

Figure 4B:
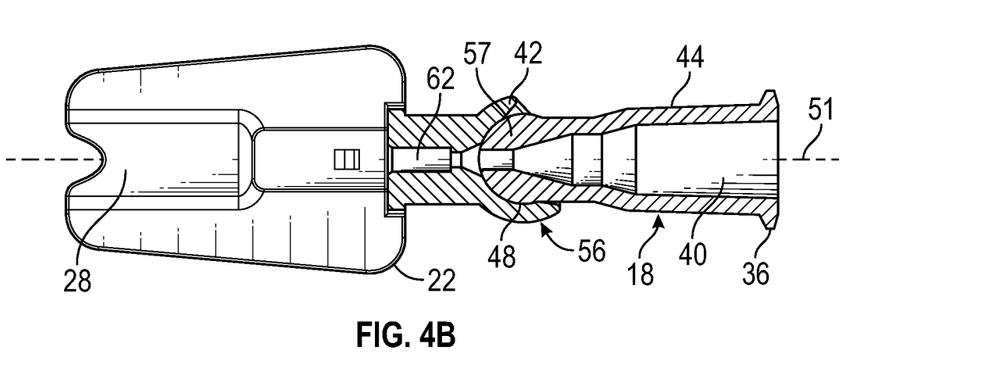
FIG. 4B is a cross-sectional view of the support device of FIG. 4A, illustrating the other valve in the first position, according to some embodiments.
Figure 4C:
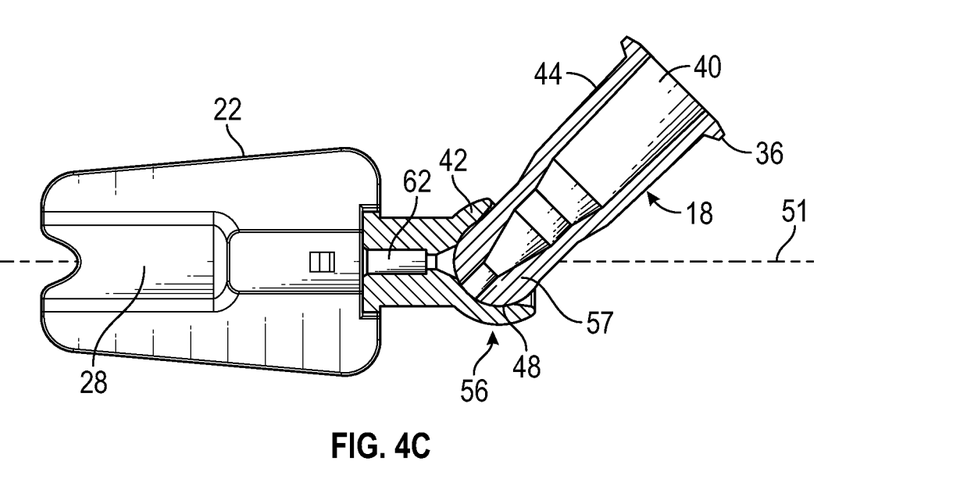
FIG. 4C is a cross-sectional view of the support device of FIG. 4A, illustrating the other valve in the second position, according to some embodiments.
Figure 4D:
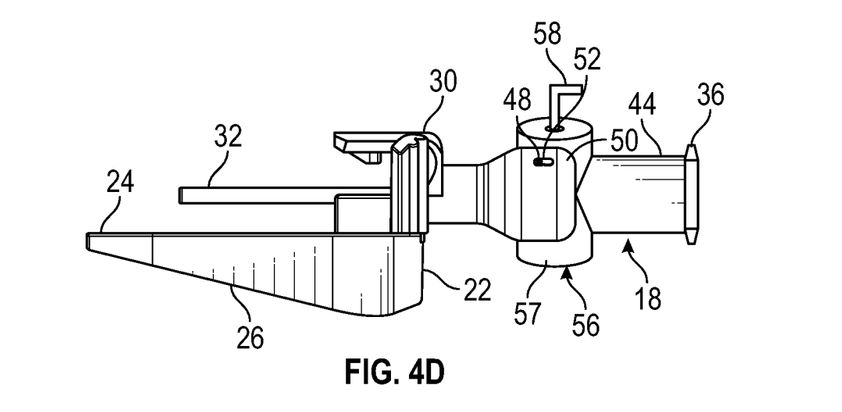
FIG. 4D is a side view of the support device of FIG. 4A, illustrating the alignment mechanism, according to some embodiments.

Referring now to FIGS. 4B-4D, in some embodiments, the cylinder portion 57 may include the protrusion 48. In some embodiments, the socket 42 may include the slot 50. In response to the valve 56 being moved to the first position, the protrusion 48 may be disposed at the first end of the slot 50 and/or in response to the valve 56 being moved to the second position, the protrusion 48 may be disposed at the second end of the slot 50. It is understood that, in some embodiments, an inner surface of the socket 42 may include the protrusion 48, and the outer surface of the cylinder portion 57 may include the slot 50.

In some embodiments, the slot 50 may include the neck portion 52. In some embodiments, the socket 42 may be asymmetrical, and may limit motion of the valve 56 to the first position, the second position, and an angle in between the first position and the second position. In some embodiments, the socket 42 may include the protrusions 53, which may contact the outer surface of the cylinder portion 57 to provide resistance to moving the valve 56 between the first position and the second position. In some embodiments, the cylinder portion 57 may include the protrusions 53, which may contact the socket 42 and provide resistance to moving the valve 56 between the first position and the second position.

In some embodiments, the cylinder portion 57 may include the handle 58, which may be disposed on an exterior surface of the valve 56. In some embodiments, the handle 58 may include a rigid bar, a generally cylindrical grip, or any suitable handle. In response to rotation of the handle 58 a predetermined amount, the valve 56 may move between the first position and the second position. In some embodiments, the cylinder portion 57 may include a position indicator (not illustrated) disposed on an exterior surface of the valve 56 to provide an indication of the position of the valve 56. In some embodiments, the protrusion 48 and a position of the protrusion 48 in the slot 50 may provide an indication of the position of the valve 56.

In some embodiments, the extension element 18 may include any suitable type of valve. In some embodiments, the extension element 18 may include a stem valve. In some embodiments, the arm 44 may not move in order to open and close a particular valve of the extension element 18.

Figure 5:
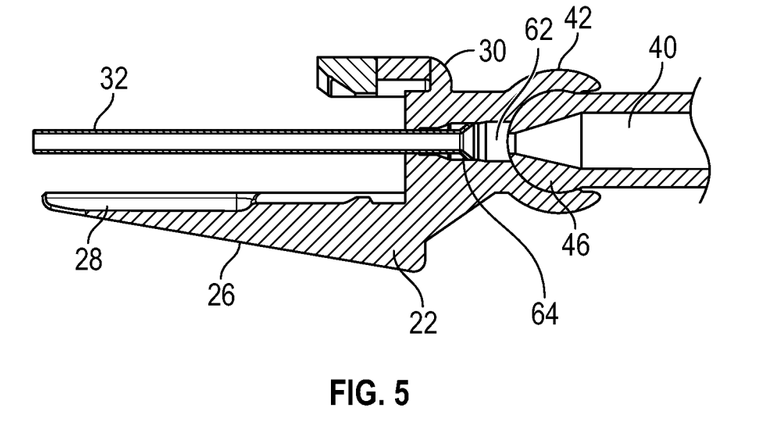
FIG. 5 is a cross-sectional view of the support device of FIG. 1A, illustrating an example cannula and example pocket configured to receive the cannula, according to some embodiments.

Referring now to FIG. 5, in some embodiments, the support device 10 may include a fluid pathway 40 therethrough. In some embodiments, the support device 10 may further include a pocket 62. In some embodiments, the cannula 32 may be secured within the pocket 62. In some embodiments, the cannula 32 may be swaged into the pocket 62. In some embodiments, swaging may include driving the cannula 32 into the pocket 62 to create an air-tight and water-tight seal and mechanical bond between the cannula 32 and the pocket 62. In some embodiments, a cone-shaped section of the pocket 62 may dig into a proximal end of the cannula 32, which may create positional locking of the cannula 32 within the pocket 62. In some embodiments, a portion of the pocket 62 distal to the cone-shaped section may interfere with the cannula 32, which may support any rotational torques applied to the cannula 32. In these embodiments, swaging may include changing dimensions of the cannula 32 by forcing the cannula 32 into a die. In some embodiments, swaging may create a groove, ridge, or shape on the cannula 32 by forming it with a mold.

In some embodiments, in response to the cannula 32 being swaged into the pocket 62, a fluid-tight and an air-tight seal may be provided between the cannula 32 and the pocket 62 such that fluid may not pass between a wedge 64 and a surface of the pocket 62. In some embodiments, the pocket 62 may not include adhesive. In some embodiments, the cannula 32 secured within the pocket 62 without adhesive and/or without ultraviolet curing. In some embodiments, the cannula 32 may be secured within the pocket via one or more of the following: swaging, adhesive, and ultraviolet curing.

Figure 6A:
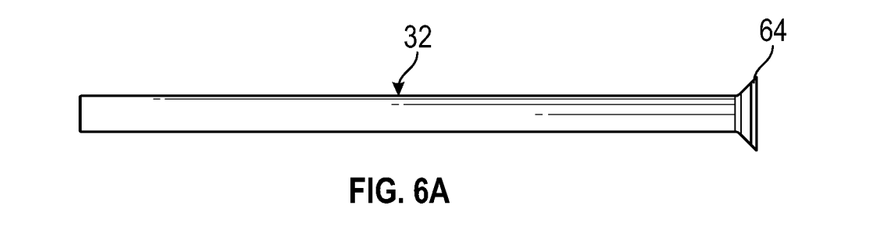
FIG. 6A is a side view of the cannula of FIG. 5, according to some embodiments.
Figure 6B:
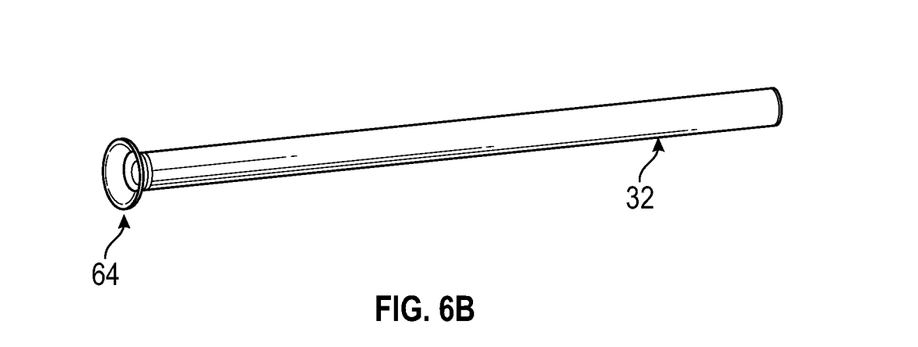
FIG. 6B is an upper perspective view of the cannula of FIG. 5, according to some embodiments.

Referring now to FIGS. 6A-6B, in some embodiments, the cannula 32 may include a distal end, a proximal end, and a lumen extending through the distal end of the cannula 32 and through the proximal end of the cannula 32. In some embodiments, the cannula 32 may include a plastic or a metal material.

In some embodiments, the proximal end of the cannula 32 may include the wedge 64. In some embodiments, the wedge 64 may be formed by deep drawing. In further detail, in some embodiments, deep drawing may begin with a blank, which may be flat, disc-shaped, or another suitable shape. In some embodiments, the blank may then be placed over a die or cavity and a punch portion of a machining tool may force the blank through the die, forming the cannula 32 and/or the wedge 64. In some embodiments, the blank may include a cannula shape or a tube shape. In some embodiments, the blank may undergo plastic deformation to form the wedge 64.

In some embodiments, the wedge 64 may be manufactured by other processes, which may include one or more of the following: stamping, coating, or three-dimensional printing. In some embodiments, a length and/or diameter of the wedge 64 may vary to provide more lead in material or a larger securement area. In some embodiments, the distal end of the cannula 32 may be blunt or may include a rounded tip. In some embodiments, the distal end of the cannula 32 may be sharp. In some embodiments, a shape of the cannula 32 may vary.

Figure 6C:
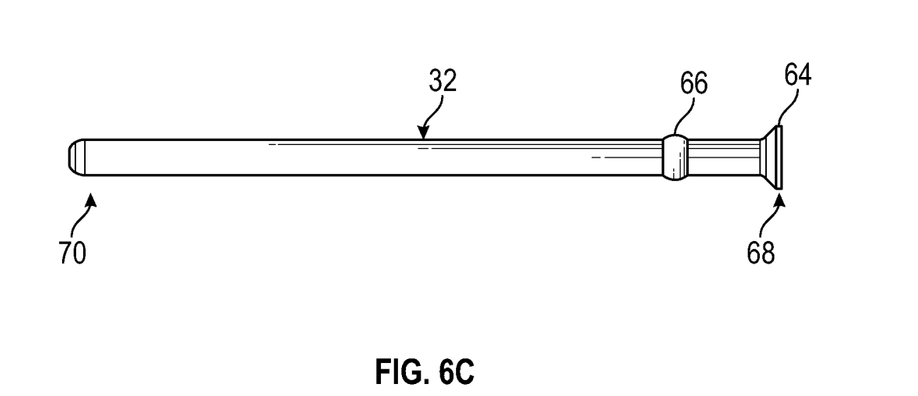
FIG. 6C is a side perspective view of the cannula of FIG. 5, illustrating an example protrusion on an outer surface of the cannula, according to some embodiments.

Referring now to FIG. 6C, in some embodiments, after the cannula 32 is swaged and secured within the pocket 62, one or more post-processing steps may occur. For example, the cannula 32 may be forced into a die to form a retaining feature, such as a protrusion 66, a bump, a retaining ring, a groove, a ridge, or another geometry on the cannula 32 distal to the extension element 18.

In some embodiments, the retaining feature may not fit through the portion of the pocket 62 distal to the cone-shaped section that interferes with the cannula 32. In some embodiments, the retaining feature may be configured to engage with a protective cover to protect a lubrication film of the cannula 32, to provide sterility and cleanliness to the cannula 32, and/or to protect the clinician and the patient from being "stuck" with the cannula 32. In some embodiments, the retaining feature may be configured to secure the cannula 32 within the extension element 18 or to secure the cannula 32 within the catheter assembly 12. In some embodiments, the retaining feature may be used to secure the cannula 32 to other medical devices. In some embodiments, the retaining feature may include a hook or barb, which may secure the cannula 32 within the catheter assembly 12 and/or another medical device.

In some embodiments, the protrusion 66 may be annular. In some embodiments, the cannula 32 may include a first outer diameter at the proximal end 68 of the cannula 32 and a second outer diameter at the distal end 70 of the cannula 32. In some embodiments, the first diameter may be greater than the second diameter. In some embodiments, the first diameter and the second diameter may be manufactured by deep drawing. In some embodiments the first diameter and the second diameter may be formed by one or more of the following: stamping, coating, three dimensional printing, bonding, and another suitable method. In some embodiments, multiple parts may be assembled or bonded together to form the cannula 32. In some embodiments, the cannula 32 may include more than one protrusion 66. In some embodiments, a method of securing the cannula 32 within the support device 10 may include providing the cannula 32. In some embodiments, the method may include forming the protrusion 66 on an exterior surface of the cannula 32.

In some embodiments, the cannula 32 may include a lubricant and/or an adhesive applied to an exterior surface of the cannula 32. In some embodiments, the lubricant and/or the adhesive may be cured. In some embodiments, the method may include applying the lubricant and/or the adhesive to the cannula 32.

In some embodiments, the method may include forming the wedge 64 at the proximal end of a cannula 32 by deep drawing or other methods. In some embodiments, the method may include providing a medical device, within which the proximal end of the cannula 32 may be secured. In some embodiments, the medical device may include the support device 10 or another suitable device. In some embodiments, the medical device may include a needle assembly, a syringe, or another suitable device to facilitate blood draw.

In some embodiments, the medical device may include the pocket 62, which may be configured to receive the proximal end 68 of the cannula 32. In some embodiments, the proximal end 68 of the cannula 32 may be inserted into the pocket 62, and the cannula 32 may then be swaged such that the proximal end 68 of the cannula 32 may be seated into the pocket 62. In some embodiments, the wedge 64 may provide a fluid seal after the cannula 32 is swaged into the pocket 62. In some embodiments, the method may include providing one or more other medical devices, which may be coupled to the medical device to provide a fluid path through the medical device and the other medical devices. In some embodiments, the other medical device may include the catheter assembly 12.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A support device to support a catheter assembly, the support device comprising:
   a platform having an upper surface and a bottom surface, wherein the bottom surface is configured to contact skin of a patient, wherein at least a portion of the upper surface is configured to support a catheter assembly;
   an extension element coupled to the upper surface of the platform, wherein the extension element comprises:
      a distal end, comprising a first connector configured to couple to the catheter assembly;
      a proximal end, comprising a second connector; and
      a valve disposed between the distal end and the proximal end, wherein the valve is movable between a first position and a second position; and
      a cannula extending distally from the distal end of the extension element and secured within the extension element,
   wherein in response to the valve being moved to the first position, a fluid pathway extending through the cannula and the extension element is open and straight, wherein in response to the valve being moved to the second position, the fluid pathway is closed, wherein the valve comprises a socket and an arm, wherein the arm comprises a distal end, a proximal end, and a lumen extending through the distal end of the arm and the proximal end of the arm, wherein the distal end of the arm comprises a ball portion configured to rotate within the socket, wherein the proximal end of the arm comprises the second connector.

2. The support device of claim 1, wherein an outer surface of the ball portion comprises a protrusion, wherein the socket comprises a slot, wherein the slot comprises a first end and a second end, wherein in response to the valve being moved to the first position, the protrusion is disposed at the first end of the slot, wherein in response to the valve being moved to the second position, the protrusion is disposed at the second end of the slot.

3. The support device of claim 2, wherein the slot comprises a neck portion, wherein in response to the valve being moved to the first position, the protrusion passes through the neck portion and provides an audible indication.

4. The support device of claim 1, wherein the socket comprises a plurality of protrusions that contact an outer surface of the arm, wherein the plurality of protrusions are configured to provide resistance in moving the valve from the first position to the second position.

5. The support device of claim 1, wherein the cannula comprises a distal end, a proximal end, and a lumen extending there through, wherein the proximal end of the cannula comprises a wedge.

6. The support device of claim 1, wherein the cannula is swaged into the extension element.

7. The support device of claim 1, wherein the valve comprises a socket and an arm, wherein the arm comprises a distal end, a proximal end, and a lumen extending through the distal end of the arm and the proximal end of the arm, wherein the distal end of the arm comprises a generally cylindrical shape configured to rotate within the socket, wherein the socket is generally cylindrical, wherein the proximal end of the arm comprises the second connector.

8. The support device of claim 1, wherein an outer surface of the cannula comprises a protrusion.

9. The support device of claim 1, wherein the platform is wedge-shaped.

10. The support device of claim 1, wherein the portion of the upper surface comprises a groove configured to support a catheter adapter of the catheter assembly.

11. The support device of claim 1, wherein the first connector comprises a snap feature, wherein the snap feature comprises an arm, wherein the arm comprises a protrusion.

12. A method of securing a cannula, comprising:
   providing a cannula, wherein the cannula comprises a distal end, a proximal end, and a lumen extending through the distal end and the proximal end;
   forming a wedge at the proximal end of a cannula;
   providing a medical device, wherein the medical device comprises a pocket configured to receive the proximal end of the cannula;
   inserting the proximal end of the cannula into the pocket; and swaging the proximal end of the cannula into the pocket, wherein the medical device comprises a support device to support a catheter assembly, the support device comprising:

a platform, comprising an upper surface and a bottom surface, wherein the bottom surface is configured to contact skin of a patient, wherein at least a portion of the upper surface is configured to support a catheter assembly; and an extension element coupled to the upper surface of the platform, wherein the extension element comprises:

a distal end, comprising a first connector configured to couple to the catheter assembly; and a proximal end, comprising a second connector;

the pocket disposed between the distal end and the proximal end.

13. The method of claim 12, wherein the wedge provides a fluid seal after the cannula is swaged into the pocket.

14. The method of claim 12, wherein forming the wedge at the proximal end of the cannula comprises deep drawing, stamping, coating, or three-dimensional printing.

15. The method of claim 12, wherein the extension element comprises a valve, wherein the valve comprises an arm, wherein in response to movement of the arm, the valve is configured to move between a first position and a second position.

16. The method of claim 15, wherein a distal end of the arm comprises a ball portion, a cylinder portion, or a plurality of flat surfaces.

* * * * *